United States Patent [19]
Rufenacht

[11] 3,935,224
[45] Jan. 27, 1976

[54] 4H-PYRIDO[3,2A]-1,3,2-DIOXOPHOSPHORANE DERIVATIVES

[75] Inventor: Kurt Rufenacht, Basel, Switzerland

[73] Assignee: Ciba-Geigy Corporation, Ardsley, N.Y.

[22] Filed: Nov. 1, 1972

[21] Appl. No.: 302,641

[30] Foreign Application Priority Data
Dec. 10, 1971 Switzerland.................. 18066/71
Sept. 15, 1972 Switzerland.................. 13544/72

[52] U.S. Cl.................. 260/294.8 C; 260/294.8 K; 260/296 B; 260/297 B; 424/263
[51] Int. Cl.$^2$.................................... C07D 213/71
[58] Field of Search.............. 260/294.8 C, 297 B

[56] References Cited
UNITED STATES PATENTS
3,094,458 6/1963 Chiddix et al. .................. 260/936

OTHER PUBLICATIONS
Houben-Weyl, Methoden Der Organischen Chemie, Band XII/2, Verlag Pub., pp. 241 and 321.

Primary Examiner—Alan L. Rotman
Attorney, Agent, or Firm—Harry Falber; Frederick H. Rabin

[57] ABSTRACT

4H-pyrido[3,2-a]-1,3,2-dioxaphosphorin compounds of the formula

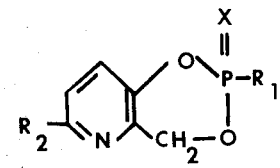

wherein $R_1$ represents $C_1$–$C_5$ alkyl, $C_1$–$C_5$ alkoxy, $C_3$–$C_4$ alkenyloxy, $C_3$–$C_4$ alkinyloxy, $C_1$–$C_5$ alkylthio, phenoxy, phenyl, amino, $C_1$–$C_5$ alkylamino, ($C_1$–$C_5$ alkyl)$_2$amino or halogen, $R_2$ represents hydrogen or $C_1$–$C_5$ alkyl and X represents oxygen or sulphur.

4 Claims, No Drawings

4H-PYRIDO[3,2A]-1,3,2-DIOXOPHOSPHORANE DERIVATIVES

The present invention relates to 4H-pyrido[3,2-a]-1,3,2-dioxaphosphorin compounds, a process for their manufacture, and to their use in pest control.

The active substances according to the invention have the formula (I)

wherein $R_1$ represents $C_1-C_5$ alkyl, $C_1-C_5$ alkoxy, $C_3-C_4$ alkenyloxy, $C_3-C_4$ alkinyloxy, $C_1-C_5$ alkylthio, phenoxy, phenyl, amino, $C_1-C_5$ alkylamino, $(C_1-C_5$ alkyl)$_2$amino or halogen, $R_2$ represents hydrogen or $C_1-C_5$ alkyl and X represents oxygen or sulphur.

By halogen is menat in this connection fluorine, chlorine, bromine or iodine, in particular chlorine.

The phenyl or phenoxy radical represented by $R_1$ may be unsubstituted or mono- or polysubstituted by e.g. fluorine, chlorine, bromine, iodine, $C_1-C_5$ alkyl, —$CF_3$ or —$NO_2$.

The alkyl, alkoxy, alkylthio, alkylamino, dialkylamino, alkenyloxy and alkinyloxy groups which are eligible for $R_1$ and $R_2$ may be straight-chain or branched, substituted or unsubstituted. Suitable substituents at these groups are, for example, halogen and alkoxy.

Examples of such groups include: methyl, methoxy, methylthio, methylamino, dimethylamino, ethyl, ethoxy, ethylthio, ethylamino, diethylamino, propyl, propoxy, propylthio, isoptopyl, isopropxy, isopropylthio, n-, i-, sec. and tert.butyl, n-butoxy, n-butylthio, n-pentyl and the isomers thereof, allyloxy, methallyloxy, propargyloxy.

On account of their action, preferred compounds are those of the formula I, wherein $R_1$ represents methyl, ethyl, $C_1-C_4$ alkoxy, $C_1-C_4$ alkylthio, $C_3-C_4$ alkenyloxy, $C_3-C_4$ alkinyloxy, phenoxy, phenyl, amino, $C_1-C_5$ alkylamino, $(C_1-C_3$ alkyl)$_2$amino or halogen, $R_2$ represents methyl and X represents oxygen or sulphur.

The compounds of the formula I can be manufactured by the following methods which are known per se: a) directly, for all means of $R_1$ (II)   (III)

b) indirectly, for those cases in which $R_1$ is alkoxy, alkylthio, alkenyloxy, alkinyloxy, phenoxy, amino, alkylamino or dialkylamino.

(II)   (IV)

$b_1$ salt of compound VI
(V)

$b_1$ + $R_1H$ (VI) + 1 mole of acid binding agent;
if $R_1$ is amino, alkylamino or dialkylamino:
2 moles of $R_1H$ if $R_1$ is alkoxy, alkylthio, alkenyloxy, alkinyloxy, phenoxy.

In the formulae II to VI, the symbols $R_1$, $R_2$ and X have the meaning indicated for the formula I.

Suitable salts of the compound VI for the process $b_2$ are, for example, salts of monovalent metals, in particular alkali metal salts.

The following bases, for example, are suitable as acid binding agents: tertiary amines, such as triethylamine, dimethylaniline, pyridine, inorganic bases, such as hydroxides and carbonates of alkali and alkaline earth metals, preferably sodium and potassium hydroxide.

The reaction is carried out preferably in solvents or diluents which are inert towards the reactants or in an excess of a tertiary amine, e.g. pyridine. Suitable inert solvents or diluents are, for example, the following: aromatic hydrocarbons, such as benzene, toluene, benzines, halogenated hydrocarbons, chlorobenzene, polychlorobenzenes, bromobenzene, chlorinated alkanes with 1 to 3 carbon atoms, ethers, such as dioxan, tetrahydrofuran; esters, such as ethyl acetate; ketones, such as methyl ethyl ketone, diethyl ketone, nitriles etc.

Some of the starting materials of the formula I are known compounds which can be manufactured by methods which are known per se (cf. Kato et al., Chem. Abstr. 59, 559e (1963)).

The compounds of the formulae III and IV are known or they may be manufactured by methods which are known per se in analogous manner. The compounds of the formula I display a broad biocidal activity and are therefore suitable for combating various plant and animal pests.

In particular, the compounds of the formula I possess insecticidal and acaricidal properties and may be used against all development stages, e.g. eggs, larvae, pupae, nymphs and adults, of insects and representatives of the order Acarina, for example against insects of the families:

Tettigonidae
Tenebrionidae
Gryllidae
Chrysomelidae
Gryllotalpidae
Bruchidae
Blattidae
Tineidae
Reduviidae
Noctindae
Phyrrhocoriae
Lymatriidae
Cimicidae
Pyralidae
Delphacidae
Culicidae
Aphididae
Tipulidae
Diaspididae
Stomoxydae
Pseudococcidae
Trypetidae
Scarabaeidae
Muscidae
Dermestidae
Calliphoridae and
Coccinellidae
Pulicidae Acarida of the families:
Ixodidae
Argasidae
Tetranychidae and
Dermanyssidae.

The insecticidal and/or acaricidal action can be substantially broadened and adapted to suit the particular circumstances by the addition of other insecticides and/or acaricides.

Suitable additives include, for example, the following active substances:

Bis-0,0-diethylphosphoric acid anhydride (TEPP)
Dimethyl-(2,2,2-trichloro-1-hydroxyethyl)-phosphonate (TRICHLORFON)
1,2-dibromo-2,2-dichloroethyldimethylphosphate (NALED)
2,2-dichlorovinyldimethylphosphate (DICHLORVOS)
2-methoxycarbamyl-1-methylvinyldimethylphosphate (MEVINPHOS)
Dimethyl-1-methyl-2-(methylcarbamoyl)-vinylphosphate cis (MONOCROTOPHOS)
3-(dimethoxyphosphinyloxy)-N,N-dimethyl-cis-crotonamide (DICROTOPHOS)
2-chloro-2-diethylcarbamoyl-1-methylvinyldimethylphosphate (PHOSPHAMIDON)
0,0-diethyl-0(or S)-2-(ethylthio)-ethylthiophosphate (DEMETON)
S-ethylthioethyl-0,0-dimethyl-dithiophosphate (THIOMETON)
0,0-diethyl-S-ethylmercaptomethyldithiophosphate (PHORATE)
0,0-diethyl-S-2-ethylthio)ethyldithiophosphate (DISLUFOTON)
0,0-dimethyl-S-2-(ethylsulphinyl)ethylthiophosphate (OXYDEMETON METHYL)
0,0-dimethyl-S-(1,2-dicarbethoxyethyldithiophosphate (MALATHION)
0,0,0,0-tetraethyl-S,S'-methylene-bis-dithiophosphate (ETHION)
0-ethyl-S,S-dipropyldithiophosphate
0,0-dimethyl-S-(N-methyl-N-formylcarbamoylmethyl)-dithiophosphate (FORMOTHION)
0,0-dimethyl-S-(N-methylcarbamoylmethyl)dithiophosphate (DIMETHOATE)
0,0-dimethyl-0-p-nitrophenylthiophosphate (PARATHION-METHYL)
0,0-diethyl-0-p-nitrophenylthiophosphate (PARATHION)
0-ethyl-0-p-nitrophenylphenylthiophosphate (EPN)
0,0-dimethyl-0-(4-nitro-m-tolyl)thiophosphate (FENITROTHION)
0,0-dimethyl-0-2,4-5-trichlorophenylthiophosphate (RONNEL)
0-ethyl-0,2,4,5-trichlorophenylethylthiophosphate (TRICHLORONATE)
0,0-dimethyl-0-2,5-dichloro-4-bromophenylthiophosphate (BROMOPHOS)
0,0-dimethyl-0-(2,5-dichloro-4-jodphenyl)-thiophosphate (JODOFENPHOS)
4-tert. butyl-2-chlorophenyl-N-methyl-0-methylamidophosphate (CRUFOMATE)
0,0-dimethyl-0-(3-methyl-4-methylmercaptophenyl)-thiophosphate (FENTHION)
Isopropylamino-0-ethyl-0-(4-methylmercapto-3-methylphenyl)phosphate
0,0-diethyl-0-p-(methylsulphinyl)phenyl-thiophosphate (FENSULFOTHION)
0-p-(dimethylsulphamido)phenyl-0,0-dimethylthiophosphate (FAMPHUR)
0,0,0',0'-tetramethyl-0,0'-thiodi-p-phenylenethiophosphate
0-ethyl-S-phenyl-ethyldithiophosphate
0,0-dimethyl-0-(α-methylbenzyl-3-hydroxycrotonyl)-phosphate
2-chloro-1-(2,4-dichlorophenyl)vinyl-diethylphosphate (CHLORFENVINPHOS)
1-chloro-1-(2,4,5-trichlorophenyl)vinyl-dimethylphosphate
0-[2-chloro-1-(2,5-dichlorophenyl)]vinyl-0,0-diethyl-thiophosphate
Phenylglyoxylonitriloxim-0,0-diethylthiophosphate (PHOXIM)
0,0-diethyl-0-(3-chloro-4-methyl-2-oxo-2-H-1-benzopyran-7-yl)thiophosphate (COUMAPHOS)
2,3-p-dioxandithiol-S,S-bis(0,0-diethyldithiophosphate) (DIOXATHION)
5-[(6-chloro-2-oxo-3-benzoxazolinyl)methyl]0,0-diethyldithiophosphate (PHOSALONE)
2-(diethoxyphosphinylimino)-1,3-dithiolane
0,0-dimethyl-S-[2-methoxy-1,3,4-thiadiazol -5-(4H)-onyl-(4)-methyl]dithiophosphate
0,0-dimethyl-S-phthalimidomethyl-dithiophosphate (IMIDAN)
0,0-diethyl-0-(3,5,6-trichloro-2-pyridyl)thiophosphate
0,0-diethyl-0-2-pyrazinylthiophosphate (THIONAZIN)
0,0-diethyl-0-(2-isopropyl-4-methyl-6-pyrimidyl)thiophosphate (DIAZINON)
0,0-diethyl-0-(2-chinoxalyl)thiophosphate
0,0-dimethyl-S-(4-oxo-1,2,3-benzotriazin-3(4H)-ylmethyl)dithiophosphate (AZINPHOSMETHYL)
0,0-diethyl-S-(4-oxo-1,2,3-benzotriazin-3(4H)-ylmethyl)dithiophosphate (AZINPHOSETHYL)
S-[(4,6-diamino-s-triazin-2-yl)methyl]-0,0-dimethyldithiophosphate (MENAZON)

O,O-dimethyl-O-(3-chloro-4-nitrophenyl)thiophosphate (CHLORTHION)
O,O-dimethyl-O(or S)-2-(ethylthioethyl)thiophosphate (DEMETON-S-METHYL)
2-(O,O-dimethyl-phosphoryl-thiomethyl)-5-methoxy-pyron-4-3,4-dichlorobenzyl-triphenylphosphonium-chloride
O,O-diethyl-S-(2,5-dichlorophenylthiomethyl)dithiophosphate (PHENKAPTON)
O,O-diethyl-O-(4-methyl-cumarinyl-7-)-thiophosphate (POTASAN)
5-amino-bis(dimethylamido)phosphinyl-3-phenyl-1,2,4-triazole (TRIAMIPHOS)
N-methyl-5-(O,O-dimethylthiolphosphoryl)-3-thiavaleramide (VAMIDOTHION)
O,O-diethyl-O-[2-diemthylamino-4-methylpyrimidyl-(6)]-thiophosphate (DIOCTHYL)
O,O-dimethyl-S-(methylcarbamoylmethyl)-thiophosphate (OMETHOATE)
O-ethyl-O-(8-quinolinyl)-phenylthiophosphonate (OXINOTHIOPHOS)
O-methyl-S-methyl-amidothiophosphate (MONITOR)
O-methyl-O-(2,5-dichloro-4-bromophenyl)-benzothiophosphate (PHOSVEL)
O,O,O,O-tetrapropyldithiophosphate
3-(dimethoxyphosphinyloxy)-N-methyl-N-methoxy-cis-crotonamide
O,O-diemthyl-S-(N-ethylcarbamoylmethyl)dithiophosphate (ETHOATE-METHYL)
O,O-diethyl-S-(N-isopropylcarbamoylmethyl)-dithiophosphate (PROTHOATE)
S-N-(1-cyano-1-methylethyl)carbamoylmethyldiethylthiolphosphate (CYANTHOATE)
S-(2-acetamidoethyl)-O,O-dimethyldithiophosphate
Hexamethylphosphoric acid triamide (HEMPA)
O,O-dimethyl-O-(2-chloro-4-nitrophenyl)thiophosphate (DICAPTHON)
O,O-dimethyl-O-p-cyanophenyl thiophosphate (CYANOX)
O-ethyl-O-p-cyanophenylthiophosphonate
O,O-diethyl-O-2,4-dichlorophenylthiophosphate (DICHLORFENTHION)
O,2,4-dichlorophenyl-O-methylisopropylamidothiophosphate
O,O-diethyl-O-2,5-dichloro-4-bromophenylthiophosphate (BROMOPHOS-ETHYL)
Dimethyl-p-(methylthio)phenylphosphate
O,O-dimethyl-O-p-sulfamidophenylthiophosphate
O-[p-(p-chlorophenyl)azophenyl]O,O-dimethylthiophosphate (AZOTHOATE)
O-ethyl-S-4-chlorophenyl-ethyldithiophosphate
O-isobutyl-S-p-chlorophenyl-ethyldithiophosphate
O,O-dimethyl-S-p-chlorophenylthiophosphate
O,O-dimethyl-S-(p-chlorophenylthiomethyl)dithiophosphate
O,O-diethyl-p-chlorophenylmercaptomethyl-dithiophosphate (CARBOPHENOTHION)
O,O-diethyl-S-p-chlorophenylthiomethyl-thiophosphate
O,O-dimethyl-S-(carbethoxy-phenylmethyl)dithiophosphate (PHENTHOATE)
O,O-diethyl-S-(carbofluorethoxy-phenylmethyl)-dithiophoshphate
O,O-dimethyl-S-carboisopropoxy-phenylmethyl)-dithiophosphate
O,O-diethyl-7-hydroxy-3,4-tetramethylene-coumarinyl-thiophosphate (COUMITHOATE)
2-methoxy-4-H-1,3,2-benzodioxaphosphorin-2-sulphide
O,O-diethyl-O-(5-phenyl-3-isooxazolyl)thiophosphate
2-(diethoxyphosphinylimino)-4-methyl-1,3-dithiolane
Tris-(2-methyl-1-aziridinyl)-phosphine oxide (METEPA)
S-(2-chloro-1-phthalimidoethyl)-O,O-diethyldithiophosphate
N-hydroxynaphthalimido-diethylphosphate
Dimethyl-3,5,6-trichloro-2-pyridylphosphate
O,O-dimethyl-O-(3,5,6-trichloro-2-pyridyl)thiophosphate
S-2-(ethylsulphonyl)ethyl dimethylthiolphosphate (DIOXYDEMETON-S-METHYL)
Diethyl-S-2-(ethylsulphinyl)ethyl dithiophosphate (OXIDISULFOTON)
Bis-O,O-diethylthiophosphoric acid anhydride (SULFOTEP)
Dimethyl-1,3-di(carbomethoxy)-1-propen-2-yl-phosphate
Dimethyl-(2,2,2-trichloro-1-butyroyloxyethyl)phosphate (BUTONATE)
O,O-dimethyl-O-(2,2-dichloro-1-methoxy-vinyl)phosphate
Bis-(dimethylamido)fluorphosphate (DIMEFOX)
3,4-dichlorobenzyl-triphenylphosphoniumchloride
Dimethyl-N-methoxymethylcarbamoylmethyl-dithiophosphate (FORMOCARBAM)
O,O-diethyl-O-(2,2-dichloro-1-chloroethoxyvinyl)-phosphate
O,O-dimethyl-O-(2,2-dichloro-1-chloroethoxyvinyl)-phosphate
O-ethyl-S,S-diphenyldithiolphosphate
O-ethyl-S-benzyl-phenyldithiophosphonate
O,O-diethyl-S-benzyl-thiolphosphate
O,O-dimethyl-S-(4-chlorophenylthiomethyl)dithiophosphate (METHYLCARBOPHENOTHION)
O,O-dimethyl-S-(ethylthiomethyl)dithiophosphate
Diisopropylaminofluorophosphate (MIPAFOX)
O,O-dimethyl-S-(morpholinylcarbamoylmethyl)dithiophosphate (MORPHOTHION)
Bismethylamido-phenylphosphate
O,O-dimethyl-S-(benzene sulphonyl)dithiophosphate
O,O-dimethyl-(S and O)-ethylsulphinylethylthiophosphate
O,O-diethyl-O-4-nitrophenylphosphate
Triethoxy-isopropoxy-bis(thiophosphinyl)disulphide
2-methoxy-4H-1,3,2,benzodioxaphosphorin-2-oxide
Octamethylpyrophosphoramide (SCHRADAN)
Bis (dimethoxythiophospphinylsulphido)-phenylmethane
N,N,N',N'-tetramethyldiamidofluorophosphate (DIMEFOX)
O-phenyl-O-p-nitrophenyl-methanthiophosphonate (COLEP)
O-methyl-O-(2-chloro-4-tert.butyl-phenyl)-N-methylamidothiophosphate (NARLENE)
O-ethyl-O-(2,4-dichlorophenyl)-phenylthiophosphonate
O,O-diethyl-O-(4-methylmercapto-3,5-dimethylphenyl)-thiophosphate
4,4'-bis-(O,O-dimethylthiophosphoryloxy)-diphenyl disulphide
O,O-di-($\beta$-chloroethyl)-O-(3-chloro-4-methylcoumarinyl-7)-phosphate
S-(1-phthalimidoethyl)-O,O-diethyldithiophosphate
O,O-dimethyl-O-(3-chloro-4-diethylsulphamylphenyl)-thiophosphate
O-methyl-O-(2-carbisopropoxyphenyl)-amidothiophosphate 5-(O,O-dimethylphosphoryl)-6-chloro-bicyclo(3.2.0)-heptadiene (1,5)
O-methyl-O-(2-i-propoxycarbonyl-1-methylvinyl)-ethylamidothiophosphate.

Nitrophenols and derivatives 4,6-dinitro-6-methylphenol, Na-salt [Dinitrocresol]
dinitrobutylphenol-(2,2′,2″-triethanolamine salt
2-cyclohexyl-4,6-dinitrophenyl [Dinex]
2-(1-methylheptyl)-4,6-dinitrophenyl-crotonate [Dinocap]
2-sec.-butyl-4,6-dinitrophenyl-3-methyl-butenoate [Binapacryl]
2-sec.-butyl-4,6-dinitrophenyl-cyclopropionate
2-sec.-butyl-4,6-dinitrophenylisopropylcarbonate [Dinobuton]

Miscellaneous pyrethin I
pyrethin II
3-allyl-2-methyl-4-oxo-2-cyclopentan-1-yl-chrysanthemumate (Allethrin)
6-chloriperonyl-chrysanthemumate (Barthrin)
2,4-dimethylbenzyl-chrysanthemumate (Dimethrin)
2,3,4,5-tetrahydrophthalimidomethylchrysanthemumate
4-chlorobenzyl-4-chlorophenylsulphide [Chlorobensid]
6-methyl-2-oxol, 3-dithiolo-[4,5-b]-quinoxaline [Quinomethionate]
(I)-3-(2-furfuryl)-2-methyl-4-oxocyclopent-2-enyl(I)-cis+trans)chrysanthemum-monocarboxylate [Furethrin]
2-pivaloyl-indane-1,3-dione [Pindon]
N′-(4-chloro-2-methylphenyl)-N,N-dimethylformamidine [Chlorophenamidin]
4-chlorobenzyl-4-fluorophenyl-sulphide [Fluorobenside]
5,6-dichloro-1-phenoxycarbanyl-2-trifluoromethyl-benzimidazole [Fenozaflor]
p-chlorophenyl-p-chlorobenzenesulphonate [Ovex]
p-chlorophenyl-benzenesulphonate [Fenson]
p-chlorophenyl-2,4,5-trichlorophenylsulphone [Tetradifon]
p-chlorophenyl-2,4,5-trichlorophenylsulphide [Tetrasul]
p-chlorobenzyl-p-chlorophenylsulphide [Chlorobenside]
2-thio-1,3-dithiolo-(,5-6)-quinoxaline [Thiochinox]
prop-2-ynyl-(4-t-butylphenoxy)-cyclohexylsulphite [Propargii].

Formamidines 1-dimethyl-2-(2′-methyl-4′-chlorophenyl)-formamidine (CHLORPHENAMIDIN)
1-methyl-2-(2′-methyl-4′-chlorophenyl)-formamidine
1-methyl-2-(2′-methyl-4′-bromophenyl)-formamidine
1-methyl-2-(2′,4′-dimethylphenyl)-formamidine
1-n-butyl-1-methyl-2-(2′-methyl-4′-chlorophenyl)-formamidine
1-methyl-1-(2′-methyl-4′-chloroaniline-methylene)-formamidine
2-(2″-methyl-4″-chlorophenyl)-formamidine
1-n-butyl-2-(2′-methyl-4′-chlorophenyl-imino)-pyrolidine.

Urea

N-2-methyl-4-chlorophenyl-N′,N′-dimethyl-thiourea.

Carbamate 1-naphthyl-N-methylcarbamate (CARBARYL)
2-butinyl-4-chlorophenylcarbamate
4-dimethylamino-3,5-xylyl-N-methylcarbamate
4-dimethylamino-3-tolyl-N-methylcarbamate (AMINOCARB)
4-methylthio-3,5-xylyl-N-methylcarbamate (METHIOCARB)
3,4,5-trimethylphenyl-N-methylcarbamate
2-chlorophenyl-N-methylcarbamate (CPMC)
5-chloro-6-oxo-2-norborane-carbonitrile-O-)methylcarbamoyl)oxime
1-(dimethylcarbamoyl)-5-methyl-3-pyrazolyl-N,N-dimethylcarbamate (DIMETILAN)
2,3-dihydro-2,2-dimethyl-7-benzofuranyl-N-methylcarbamate (CARBOFURAN)
2-methyl-2-methylthio-propionaldehyde-O-(methylcarbamoyl)oxime (ALDICARB)
8-chinaldyl-N-methylcarbamate and their salts
methyl 2-isopropyl-4-(methylcarbamoyloxy)carbanilate
m-(1-ethylpropyl)phenyl-N-methylcarbamate
3,5-di-tert.butyl-N-methylcarbamate
m-(1-methylbutyl)phenyl-N-methylcarbamate
2-isopropylphenyl-N-methylcarbamate
2-sec.butylphenyl-N-methylcarbamate
m-tolyl-N-methylcarbamate
2,3-xylyl-N-methylcarbamate
3-isopropylphenyl-N-methylcarbamate
3-tert.butylphenyl-N-methylcarbamate
3-sec.butylphenyl-N-methylcarbamate
3-isopropyl-5-methylphenyl-N-methylcarbamate (PROMECARB)
3,5-diisopropylphenyl-N-methylcarbamate
2-chloro-5-isopropylphenyl-N-methylcarbamate
2-chloro-4,5-dimethylphenyl-N-methylcarbamate
2-(1,3-dioxolan-2-yl)phenyl-N-methylcarbamate (DIOXACARB)
2-(4,5-dimethyl-1,3-dioxolan-2-yl)phenyl-N-methylcarbamate
2-(1,3-dioxolan-2-yl)phenyl-N,N-dimethylcarbamate
2-(1,3-dithiolan-2-yl)-N,N-dimethylcarbamate
2-(1,3-dithiolan-2-yl)phenyl-N,N-dimethylcarbamate
2-isopropoxyphenyl-N-methylcarbamate (APROCARB)
2-(2-propinyloxy)phenyl-N-methylcarbamate
3-(2-propinyloxy)phenyl-N-methylcarbamate
2-dimethylaminophenyl-N-methylcarbamate
2-diallylaminophenyl-N-methylcarbamate
4-diallylamino-3,5-xylyl-N-methylcarbamate (ALLYXICARB)
4-benzothienyl-N-methylcarbamate
2,3-dihydro-2-methyl-7-benzofuranyl-N-methylcarbamate
3-methyl-1-phenylpyrazol-5-yl-N,N-dimethylcarbamate
1-isopropyl-3-methylpyrazol-5-yl-N,N-dimethylcarbamate (ISOLAN)
2-dimethylamino-5,6-dimethylpyrimidin-4-yl-N,N-dimethyl-carbamate
3-methyl-4-dimethylaminomethyleneiminophenyl-N-methylcarbamate
3-dimethylamino-methyleneiminophenyl-N-methylcarbamate (FORMETANATE) and their salts
1-methylthio-ethylimino-N-methylcarbamate (METHOMYL)
2-methylcarbamoyloximino-1,3-dithiolane 5-methyl-2-methylcarbamoyloximino-1,3-oxythiolane
2-(1-methoxy-2-propoxy)phenyl-N-methylcarbamate
2-(1-butin-3-yl-oxy)phenyl-N-methylcarbamate
1-dimethylcarbamyl-1'-methylthio-O-methylcarbamyl-formoxime
1-(2'-cyanoethylthio)-O-methylcarbamyl-acetaldoxime
1-methylthio-O-carbamyl-acetaldoxime
O-(3-sec.butylphenyl)-N-phenylthio-N-methylcarbamate
2,5-dimethyl-1,3-dithioland-2-(O-methylcarbamyl)-aldoxime)
O-2-diphenyl-N-methylcarbamate
2-(N-methylcarbamyl-oximino)-3-chloro-bicyclo[2.2.1]heptane
2-(N-methylcarbamyl-oximino)-bicyclo[2.2.1]heptane
3-isopropylphenyl-N-methyl-N-chloroacetyl-carbamate
3-isopropylphenyl-N-methyl-N-methylthiomethyl-carbamate
O-(2,2-dimethyl-4-chloro-2,3-dihydro-7-benzofuranyl)-N-methylcarbamate
O-(2,2,4-trimethyl-2,3-dihydro-7-benzofuranyl)-N-methylcarbamate
O-naphthyl-N-methyl-N-acetyl-carbamate
O-5,6,7,8-tetrahydronaphthyl-N-methyl-carbamate
3-isopropyl-4-methylthio-phenyl-N-methylcarbamate
3,5-dimethyl-4-methoxy-phenyl-N-methylcarbamate
3-methoxymethoxy-phenyl-N-methylcarbamate
3-allyloxyphenyl-N-methylcarbamate
2-propargyloxymethoxy-phenyl-N-methyl-carbamate
2-allyloxyphenyl-N-methyl-carbamate
4-methoxycarbonylamino-3-isopropylphenyl-N-methyl-carbamate
3,5-dimethyl-4-methoxycarbonylamino-phenyl-N-methyl-carbamate
2-γ-methylthiopropylphenyl-N-methyl-carbamate
3-(α-methoxymethyl-2-propenyl)-phenyl-N-methyl-carbamate
2-chloro-5-tert.-butyl-phenyl-N-methyl-carbamate
4-(methyl-propargylamino)-3,5-xylyl-N-methyl-carbamate
4-(methyl-γ-chloroallylamino)-3,5-xylyl-N-methyl-carbamate
4-(methyl-β-chloroallylamino)-3,5-xylyl-N-methyl-carbamate
1-(β-ethoxycarbonalethyl)-3-methyl-5-pyrazolyl-N,N-dimethylcarbamate
3-methyl-4-(dimethylamino-methylmercapto-methyleneimino)phenyl-N-methylcarbamate
1,3-bis(carbamoylthio)-2-(N,N-dimethylamino)-propanehydrochloride
5,5-dimethylhydroresorcinoldimethylcarbamate
2-[ethyl-propargylamino]-phenyl-N-methylcarbamate
2-[methyl-propargylamino]-phenyl-N-methylcarbamate
2-[dipropargylamino]-phenyl-N-methylcarbamate
4-[dipropargylamino]-3-tolyl-N-methylcarbamate
4-[dipropargylamino]-3,5-xylyl-N-methylcarbamate
2-[allyl-isopropylamino]-phenyl-N-methylcarbamate
3-[allyl-isopropylamino]-phenyl-N-methylcarbamate Chlorinated Hydrocarbons γ-hexachlorocyclohexane [GAMMEXANE; LINDAN; γ HCH]
1,2,4,5,6,7,8,8-octachloro-3α,4,7,7α'tetrahydro-4,7-methylenindane [CHLORDAN]
1,4,5,6,7,8,8-heptachloro,3α,4,7,7α-tetrahydro-4,7-methylenindane [HEPTACHLOR]
1,2,3,4,10,10-hexachloro-1,4,4α,5,8,8α-hexahydro-endo-1,4-exo-5,8-dimethanonaphthalene [ALDRIN]
1,2,3,4,10,10-hexachloro-6,7-epoxy-1,4,4α,5,6,7,8,8α-oxtahydro-exo-1,4-endo-5,8-dimethanonaphthalene [DIFLORIN]
1,2,3,4,10,10-hexachloro-5,7-epoxy-1,4,4α,5,6,7,8,8α-octyhydro-endo-endo-5,8-dimethanonaphthalene [ENDRIN]

The active substances of the formula I are also suitable for combating representatives of the division Thallophyta, e.g. viruses, bacteria and fungi. They thus possess fungicidal properties against phytophathogenic fungi on various cultivated plants, such as cereals, maize, rice, vegetables, ornamental plants, fruit trees, vines, farm products, etc.

With the new active substances it is possible to control or destroy fungi occurring on fruit, blossom, leaves, stems, tubers and roots, and from which parts of plants which grow later then also remain free. The active substances of the formula I are active in particular against phytopahtogenic fungi belonging to the following classes: Oomycetes, Zygomycetes, Ascomycetes, Basidiomycetes, Denteromycetes.

In addition, the new active substances can also be used for treating seeds, fruit, tubers etc., and the protecting them from fungus infections, for example from smut fungi of all kinds, such as Ustilaginales, e.g. Ustilago, Tilletia, Urocystis, Turbicinia and Phoma types.

In addition to the above cited acaricides and insecticides, it is also possible to admix the active substances of the formula I with, for example, bactericides, fungistatic agents, baceteriostatic agents, nematocides and-/or e.g. the following fungicides, in order to broaden the activity spectrum:

dodecylquanidine acetate (DODINE)
pentachloronitrobenzene (QUINTOZENE)
pentachlorophenol (PCP)
2-(1-methyl-n-propyl)-4,6-dinitrophenyl-2-methyl-crotonate (BINAPACRYL)
2-(1-methyl-n-heptyl)-4,6-dinitrophenylcrotonate (DINOCAP)
2,6-dichloro-4-nitroaniline (DICHLORAN)
2,3,5,6-tetrachloro-benzoquinone (1,4) (CHLORANIL)
2,3-dichloro-naphthoquinone (1,4) (DICHLONE)
N-(trichloromethylthio) phthalimide (FOLPAT)
N-(trichloromethylthio) cyclohex-4-en-1,2-dicarboximide (CAPTAN)
N-(1,1,2,2-tetrachloroethylthio)cyclohex-4-en-1,2-dicarboximide (CAPTAFOL)
N-methansulfonal-N-trichloromethylthio-chloroaniline
N'-dichlorofluoromethylthio-N,N-dimethyl-N'-phenyl-sulfamide (DICHLOFLUANID)
O-ethyl-S-benzyl-phenyldithiophosphate
O,O-diethyl-S-benzyl-thiolphosphate
disodium-ethylene-1,2-bis-dithiocarbamate (NABAM)
zinc-ethylene-1,2-bis-dithiocarbamate (ZINEB)
manganese-ethylene-1,2-bis-dithiocarbamate (polymeric) (MANEB)
tetramethylthiuramdisulfide (THIRAM)
1-oxy-3-acetyl-6-methyl-cyclohexene-(5)dione-(2,4) (DEHYDROACETIC ACID)
8-hydroxyquinoline (8-QUINOLINOL)
2-dimethylamino-6-methyl-5-n-butyl-4-hydroxy-pyrimidine methyl-N-benzimidazole-2-yl-N-(butylcarbamoyl)carbamate (BENOMYL)
2-ethylamino-6-methyl-5n-butyl-4-hydroxypyrimidine
2,3-dicyano-1,4-dithia-anthraquinone (DITHIANON)
2-(4-thiazolyl)-benzimidazole
3,5-dimethyltetrahydro-1,3,5-thiadiazine-2-thione (DAZOMET)
2,3-dihydro-5-carboxanilido-6-methyl-1,4-oxathine
pentachlorobenzyl alcohol.

Furthermore, the compounds of the formula I are suitable for combating plant pathogenic nematodes.

The compounds of the formula I may be used as pure active substance or together with suitable carriers and/or additives. Suitable carriers and additives can be solid or liquid and correspond to the substances conventionally used in formulation technique such, for example, as solvents dispersants, wetting agents, adhesives, thickeners, binders and/or fertilisers.

For application, the compounds of the formula I may be processed to dusts, emulsion concentrates, granules, dispersions, sprays, to solutions, or suspensions in the conventional formulation which is commonly employed in application technology. Mention may also be made of "cattle dips" and "spray races", in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances may take and be used in the following forms:

Solid forms:
Dusts, tracking agents, granules, coated granules, impregnated granules and homogeneous granules.

Liquid forms:
a. active substances which are dispersible in water: wettable powders, pasts, emulsions;
b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used alone or in admixture with one another.

Granules can be very easily manufactured by dissolving an active substance of the formula I in an organic solvent and applying the resulting solution to a granulated material, for example attapulgite, $SiO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk density of 300 g/litre to 600 g/litre can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilize the active substance and/or non-ionic, anionic and cationic surface active substances, which, for example, improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivates (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilize the active substance, surface-active substance and anti-foam agents and, optionally, solvents.

Wettable powders and pastes are obtained by mixing and grinding the active substances with dispersing agents and pulverulent carriers in suitable apparatus until homogeneity is attained. Suitable carriers are, for example, those mentioned for the solid forms of application. In some cases it is advantageous to use mixtures of different carriers. As dispersing agents there can be used, for example, condensation products of sulfonated naphthalene and sulfonated naphthalene derivatives with formaldehyde, condensation products of naphthalene or naphthalene sulfonic acids with phenol and formaldehyde, as well as alkali, ammonium and alkaline earth metal salts of lignin sulfonic acid, in addition, alkylaryl sulfonates, alkali and alkaline earth metal salts of dibutyl naphthalene sulfonic acid, fatty alcohol sulfates such as salts of sulfated hexadecanols, heptadecanols, octadecanols, and salts of sulfated fatty alcohol glycol ethers, the sodium salt of oleoyl ethionate, the sodium salt of oleoyl methyl tauride, ditertiary acetylene glycols, dialkyl dilauryl ammonium chloride and fatty acid alkali and alkaline earth metal salts.

Suitable anti-foam agents are silicones.

The active substances are mixed, ground, sieved and strained with the additives cited hereinabove in such a manner that, in wettable powders, the solid particle size of from 0.02 to 0.04 and in pastes, of 0.03 is not exceeded. To produce emulsifiable concentrates and pastes, dispersing agents such as those cited above, organic solvents and water are used. Examples of suitable solvents are: alcohols, benzene, xylene, toluene, dimethyl sulfoxide, and mineral oil fractions boiling between 120° and 350°C. The solvents must be practically odourless, not phytotoxic, inert to the active substances.

Furthermore, the agents according to the invention can be applied in the form of solutions. For this purpose the active substance or several active substances of the general formula I are dissolved in suitable organic solvents, mixtures of solvents or in water. Aliphatic and aromatic hydrocarbons, chlorinated derivatives thereof, alkyl naphthalenes, and mineral oils singly or in admixture with each other, can be used as organic solvents.

The content of active substance in the above described agents is between 0.1% to 95%, in which connection it should be mentioned that, in the case of application from aircraft or some other suitable means of application, it is possible to use concentrations of up to 99.5% or even pure active substance.

The active substances of the formula I can, for example, be formulated as follows:

Dusts

The following substances are used to manufacture (a) a 5% and (b) a 2% dust:
a. 5 parts of active substance
   95 parts of talcum
b. 2 parts of active substance
   1 part of highly disperse silica
   97 parts of talcum.

The active substances are mixed with the carriers and ground.

Granules

The following substances are used to produce 5% granules:
5 parts of active substance,
0.25 parts of epichlorohydrin,
0.25 parts of cetyl polyglycol ether,
3.50 parts of polyethylene glycol,
91 parts of kaolin (particle size 0.3 - 0.8 mm).

The active substance is mixed with epichlorohydrin and dissolved with 6 parts of acetone; the polyethylene glycol and cetyl polyglycol ether are then added. The thus obtained solution is sprayed on to kaolin, and the acetone subsequently evaporated in vacuo.

Wettable powder:

The following constituents are used for the preparation of (a) a 40%, (b) and (c) a 25 %, and (d) a 10% wettable powder:
a. 40 parts of active substance,
   5 parts of sodium lignin sulphonate,
   1 part of sodium dibutyl-naphthalene sulphonate,
   54 parts of silica acid.
b. 25 parts of active substance,
   4.5 parts of calcium lignin sulphonate
   1.9 parts of Champagne chalk/hydroxyethyl cellulose mixture (1:1),
   1.5 parts of sodium dibutyl naphthalene sulphonate,
   19.5 parts of silica acid,
   19.5 parts of Champagne chalk,
   28.1 parts of kaolin.
c. 25 parts of active substance,
   2.5 parts of isooctylphenoxy-polyoxyethylene-ethanol,
   1.7 parts of Champagne chalk/hydroxyethyl cellulose mixture (1:1),
   8.3 parts of sodium aluminium silicate,
   16.5 parts of kieselguhr,
   46 parts of kaolin.
d. 10 parts of active substance,
   3 parts of a mixture of the sodium salts of saturated fatty alcohol sulphates,
   5 parts of naphthalenesulphonic acid/formaldehyde condensate,
   82 parts of kaolin.

The active substances are intimately mixed, in suitable mixers, with the additives, the mixture being then ground in the appropriate mills and rollers. Wettable powder are obtained which can be diluted with water to give suspensions of any desired concentration.

Emulsifiable concentrates:

The following substances are used to produce (a) a 10% and (b) a 25% emulsifiable concentrate:
a. 10 parts of active substance,
   3.4 parts of epoxidised vegetable oil,
   13.4 parts of a combination emulsifier consisting of fatty alcohol polyglycol ether and alkylarylsulphonate calcium salt,
   40 parts of dimethylformamide,
   43.2 parts of xylene.
b. 25 parts of active substance,
   2.5 parts of epoxidised vegetable oil,
   10 parts of an alkylarylsulphonate/fatty alcohol-polyglycol ether mixture
   5 parts of dimethylformamide,
   57.5 parts of xylene.

From these concentrates it is possible to produce, by dilution with water, emulsions of any desired concentration.

Spray:

The following constituents are used to prepare a 5% spray:
5 parts of active substance,
1 part of epichlorohydrin,
94 parts of benzine (boiling limits 160° - 190°C).

EXAMPLE 1

While cooling gently, 45 g of tiethylamine are added dropwise at 20°–30°C to a suspension of 28 g of 2-hydroxymethyl-6-methyl-3-pyridinol (Kato et al.Chem. Abstr. 59, 559e (1963) ) in 150 ml of chloroform. Then 34 g of O-methyl-thiophosphoric ester dichloride are added dropwise so rapidly that the reaction temperature remains between 30° and 35°C. The reaction mixture is stirred for 2 hours at room temperature and the solvent is then distilled off in a roatry evaporator. The oily residue is treated with 200 ml of water. Extraction with ether yields 3 g of 2-methoxy-6-methyl-4H-pyrido[3,2-e]1,3,2-dioxaphosphorin-2-sulphide.

Melting point after recrystallisation from methanol/water: 74°–75°C.

Calc.: C 41.55; H 4.36; N 6.06; P 13.42; S 13.87 %;
Found: C 41.41; H 4.30; N 6.12; P 13.32; S 13.78 %

EXAMPLE 2

To a suspension of 2-H-hydroxymethyl-6-methyl-3-pyridinol in 200 ml of chloroform are added dropwise firstly 34 g of phosphorus sulphochloride, and then slowly 42 g of triethylamine in 100 ml of chloroform. After being stirred for 1 hour at room temperature, the clear solution is treated with 400 ml of water and the mixture is concentrated in a rotary evaporator at room temperature. The crystalline precipitate of 2-chloro-6-methyl-4H-pyrido[3,2-e]1,3,2-dioxaphosphorin-2-sulphide which forms in the process is filtered off and has a melting point of 90°–91°C.

EXAMPLE 3

The 2-chloro-6-methyl-4H-pyrido[3,2-e]1,3,2-dioxaphosphorin-2-sulphide attained according to Example 2 is suspended moist in 75 ml of methanol.

While cooling, a solution of 13 g of potassium hydroxide in 75 ml of methanol is added to this suspension so rapidly that the reaction temperature remains between 10° and 15°C. Upon completion of the dropwise addition, the reaction mixture is heated briefly to 35°C and the methanol is then evaporated in a rotary evaporator at a bath temperature of 30°C. The residue is treated with water and stirred until granular crystals form. Recrystallisation from methanol/water yields 18 g of 2-methoxy-6-methyl-4H-pyrido[3,2-e]1,3,2-dioxaphosphorin-2-sulphide (m.p. 74°–75°C).

EXAMPLE 4

28 g of 2-hydroxymethyl-6-methyl-3-pyridinol are suspended in 150 ml of chloroform; then while cooling, 45 g of tiethylamine are added. Then 56 g of 2-methylthiophosphoric ester chloride are added so rapidly that the reaction temperature remains between 30° and 35°C. The reaction mixture is stirred for 2 hours at room temperature and then evaporated to dryness in a rotary evaporator at room temperature. The residue is stirred with 100 ml of water, the precipitated crystals are filtered off and recrystallised from methanol/water to give 30 g of 2-ethoxy-6-methyl-4H-pyrido[3,2-e]1,3,2-dioxaphosphorin-2-sulphide with a melting point of 54°–55°C.

Calc.: C 44.07; H 4.93; N 5.71; P 12.66; S 13.07 %;
Found: C 43.96; H 5.10; N 5.78; P 12.65; S 13.02%

EXAMPLE 5

Analogous to Example 4, 35 g of 2-hydroxymethyl-6-methyl-3-pyridinol in 180 ml of chloroform are reacted with 56 g of triethylamine and 49 g of O-isopropyl-thiophosphoric ester dichloride to give 44 g of 2-isopropoxy-6-methyl-4H-pyrido[3,2-e]-1,3,2-dioxaphosphorin-2-sulphide with a melting point of 96°–98°C.

Calc.: C 46.31; H 5.45; N 5.41; P 11.97; S 12.36 %;
Found: C 46.30; H 5.46; N 5.31; P 11.84; S 12.39 %

EXAMPLE 6

28 g of 2-hydroxymethyl-6-methyl-3-pyridinol are particularly dissolved in 100 ml of pyridine. While cooling, 30 g of methane-thiophosphonic dichloride are slowly added dropwise at 12°–25°C. The reaction mixture is stirred for 2 hours, then treated with 150 ml of water. The initially oily precipitate soon solidifies in crystalline form and is recrystallised from methanol/water to give 26 g of 2,6-dimethyl-4H-pyrido[3,2-e]-1,3,2-dioxaphosphorin-3-sulphide with a melting point at 81°–83°C.

Calc.: C 44.65; H 4.69; N 6.51; P 14.12; S 14.89 %;
Found: C 44.66; H 4.75; N 6.64; P 14.64; S 14.95 %

EXAMPLE 7

Analogous to the above Example, 35 g of 2-hydroxymethyl-6-methyl-3-pyridinol in 100 ml of pyridine are reacted with 53 g of benzene-thiophosphonic dichloride to give 45 g of 2-phenyl-6-methyl-4H-pyrido[3,2-e]1,3,2-dioxaphosphorin-2-sulphide with a melting point of 97°–98°C.

Calc.: C 56.30; H 4.37; N 5.06; P 11.19; S 11.56 %;
Found: C 56.56; H 4.43; N 5.11; P 10.90; S 11.74 %

EXAMPLE 8

In analogous manner 42 g of 2-hydroxymethyl-6-methyl-3-pyridinol in 100 ml of pyridine are reacted with 54 g of thiophosphoric dimethylamide dichloride to give 29 g of 2-dimethylamino-6-methyl-4H-pyrido[3,2-e]1,3,2-dioxaphosphorin-2-sulphide with a melting point of 101°–102°C.

Calc.: C 44.25; H 5.37; N 11.47; P 12.70; S 13.13 %;
Found: C 44.12; H 5.37; N 11.62; P 12.68; S 13.11 %

EXAMPLE 9

35 g of 2-hydroxymethyl-6-methyl-3-pyridinol are suspended in 180 ml of chloroform. Then 56 g of triethylamine are added while cooling. While cooling, 42 g of phosphoric dimethylamide dichloride are added dropwise at 30°–35°C and the reaction mixture is stirred for 2 hours at room temperature. The solvent is subsequently distilled off in a rotary evaporator and the residue dissolves to a clear solution in 60 ml of water. Exhaustive extraction with ether is performed, the ether solution dried and the ether evaporated. The oily residue crystallises on standing. Recrystallisation from ethyl acetate/petroleum ether yields 25 g of 2-dimethylamino-6-methyl-4H-pyrido[3,2-e]1,3,2-dioxaphosphorin-2-oxide with a melting point of 71°–72°C. The compound contains 1/2 water of crystallisation.

Calc.: C 45.56; H 5.95; N 11,81; P 13.06; $H_2O$ 3.79 %, Found: C 44.92; H 5.84; N 11.72; P12.99; $H_2O$ 3.38 %

EXAMPLE 10

Analogous to Example 9, 35 g of 2-hydroxymethyl-6-methyl-3-pyridinol in 180 ml of chloroform are reacted with 56 g of triethylamine and 42 g of ethane-thiophosphonic dichloride. After evaporating the solvent and additng water, an oil precipitates which is then extracted with ether and crystallises on standing. Recrystallisation from methanol/water yields 39 g of 2-ethyl-6-methyl-4H-pyrido[3,2-e]1,3,2-dioxaphosphorin-2-sulphide with a melting point of 79°–80.5°C.

Calc.: C 47.15; H 5.27; N 6.11; P 13.54; S 13.99 %;
Found: C 46.85; H 5.28; N 6.09; P 13.48; S 13.92 %

EXAMPLE 11

28 g of 2-hydroxymethyl-6-methyl-3-pyridinol are suspended in 200 ml of chloroform. To this suspension are added dropwise firstly 34 g of phosphorus sulphochloride and then, slowly, 42 g of triethylamine in 100 ml of chloroform. The clear solution is stirred for 2 hours at room temperature, then heated to 35°C and a mixture of 14 g of allyl alcohol and 20 g of triethylamine is added dropwise so rapidly that the temperature remains at 35°–37°C. The reaction mixture is stirred for 2 hours at room temperature, then the chloroform is distilled off in a rotary evaporator at 30°C. The residue is treated with 150 ml of water, in the course of which a crystalline precipitate forms. This precipitate is filtered off and recrystallised from methanol/water to give 3 g of 2-allyloxy-6-methyl-4H-pyrido[3,2-e]1,3,2-dioxaphosphorin-2-sulphide with a melting point of 79°–80°C.

Calc.: C 46,69%; H 4,71%; N 5,45%; P 12,07%; S 12,47%;

Found: C 46,38%; H 4,86%; N 5,43%; P 12,06%; S 12,43%

The following compounds are also manufactured in analogous manner to Examples 1 to 11:

2-(n)-propoxy-6-methyl-4H-pyrido[3,2-e]1,3,2-dioxaphosphorin-2-sulphide m.p.: 55°–56°C.
Calc.: C 46,31; H 5,45; N 5,41; P 11,97; S 12,36 %;
Found: C 46,72; H 5,37; N 5,61; P 12,12; S 12,54 %

2-isobutoxy-6-methoxy-4H-pyrido[3,2-e]1,3,2-dioxaphosphorin-2-sulphide m.p. 65°–66°C.
Calc.: C 48,33; H 5,90; N 5,12; P 11,36; S 11,73 %;
Found: C 48,38; H 5,87; N 4,98; P 11,48; S 11,92 %

2-propargyloxy-6-methyl-4H-pyrido[3,2-e]1,3,2-dioxaphosphorin-2-sulphide m.p. 92°–93°C.
Calc.: C 47,05; H 3,95; N 5,48; P 12,16; S 12,56 %;
Found: C 47,14; H 3,95; N 5,61; P 12,25; S 12,72 %

2-(2'-methoxy-ethoxy)-6-methyl-4H-pyrido[3,2-e]1,3,2-dioxaphosphorin-2-sulphide m.p. 64°–65°C.
Calc.: C 43,62; H 5,13; N 5,09; P 11,27; S 11,65 %;
Found: C 43,66; H 5,05; N 5,09; P 11,38; S 11,89 %

2-phenoxy-6-methyl-4H-pyrido[3,2-e]1,3,2-dioxaphosphorin-2-oxide m.p.: 148°–158,5°C.
Calc.: C 56,31; H 4,36; N 5,06; P 11,19 %; Found: C 56,24: H 4,38; N 5,06; P 11,45 %

EXAMPLE 12

A. Insecticidal ingest poison action

Tobacco and potato plants were sprayed with a 0.05% aqueous emulsion (obtained from a 10% emulsifiable concentrate).

After the coating had dried, the tobacco plants were populated with Egyptian cotton leaf worms (*Spodoptera literalis*) and the potato plants with Colorado potato beetle larvae (*Leptinotarsa decemlineata*). The test was carried out at 24°C. and 60 % relative humidity.

B. Systemic insecticidal action

To determine the systemic action, rooted bean plants (*Vicia fabae*) were put into a 0.01% aqueous active substance solution (obtained from a 10% emulsifiable concentrate). After 24 hours, aphids (*Aphis fabae*) were placed on the parts of the plant above the soil. The aphids were protected from contact and gas action by means of a special device. The test was carried out at 24°C and 70% relative humidity. In the above tests the compounds according to Example I to II displayed good insecticidal ingest poison action and systemic insecticidal action.

EXAMPLE 13

Action against Chilo suppressalis

Six rice plants at a time of the variety Caloro were transplanted into plastic pots (diameter at the top = 17 cm) and reared to a height of about 60 cm. Infestation with Chilo suppressalis larvae ($L_1$: 3–4 mm long) took place 2 days after the active substance had been applied in granule form to the paddy water (rate of application: 8 kg of active substance per hectare). Evaluation of the insecticidal action took place 10 days after application of the granules.

The compounds according to Example I to II were active in the above test against *Chilo suppressalis*.

EXAMPLE 14

Action against *Aulacophera femoralis*, *Pachmoda* and *Chortophila* larvae

Sterilised compost earth was homogeneously mixed with a wettable powder containing 25% of active substance so that there resulted a rate of application of 8 kg of active substance per hectare.

Young zucchetti plants (Cucumis pepo) were put into plastic pots with the treated soil (3plants per pot; diameter of pot = 7 cm). Each pot was infected immediately afterwards with 5 *Aulacophora femoralis* and *Pachmoda* or *Chortophila* larvae. The control was carried out 4, 8, 16 and 32 days after depositing the larvae.

At 80–100% kill after the first control, a fresh infestation with 5 larvae each was carried out in the same soil sample with 3 new zucchetti plants. If the activity was less than 80%, the remaining larvae remained in the soil sample until the control immediately following. If an active substance at a rate of application of 8 kg/ha still effected a 100% kill, a further control with 4 and 2 kg of active substance per hectare was carried out.

In the above test, the compounds according to Example I to II displayed action against *Aulacophora fermoralis*, *Pachmoda* and *Chortophila* larvae.

EXAMPLE 15

Action against ticks

A. *Rhicephalus bursa*

Five adult ticks and 50 tick larvae were counted into a glass tube and immersed for 1 to 2 minutes in 2 ml of an aqueous emulsion from an emulsion series each containing 100, 10, 1 and 0.1 ppm of test substance. The tube was then sealed with a standardised cotton wool plug and placed on its head, so that the active substance emulsion could be adsorbed by the cotton wool.

In the case of the adults evaluation took place after 2 weeks, and in that of the larvae after 2 days. Each test was repeated twice.

The compounds according to Example 1 acted in the above test against adults and larvae of *Rhicephalus bursa*.

B. *Boophilus microplus* (larvae)

Tests were carried out in each case with 20 OP-sensitive larvae using an analogous dilution series as in the case of test A. (The resistence refers to the tolerability of Diazinon).

The compounds according to Examples I to II act in the above test against sensitive and OP-resistent larvae of *Boophilus microplus*.

EXAMPLE 16

Acaracidal action

*Phaseolus vulgaris* (dwarf beans) have an infested piece of leaf from a mass culture of *Tetranychus urticae* placed on them 12 hours before the test for the acaricidal action. The mobile stages which have migrated are sprayed with the emulsified test preparations from a chromatography atomiser so that the spray broth does not run off. The number of living and dead larvae, adults and eggs are evaluated after 2 to 7 days under a stereoscopic microscope and the result expressed in percentages. During the "interim", the treated plants are kept in greenhouse compartments at 25°C.

The compounds according to Examples I and II are active in the above test against eggs, larvae and adults of *Tetranychus urticae*.

EXAMPLE 17

Action against soil nematodes

To test the action against soil nematodes, the active substance in the concentration indicated in each case is applied to and intimately mixed with soil infected with root gall nematodes (*Meloidgyne Avenaria*). Immediately afterwards, tomato cuttings are planted in the thus prepared soil in a series of tests and after a waiting time of 8 days tomato seeds are sown in another test series.

In order to assess the nematocidal action, the galls present on the roots are counted 28 days after planting and sowing respectively. The compounds according to Example I to 4 display good action against *Meloidgyne Avenaria*.

EXAMPLE 18

Fungicidal Action a. Action against *Botrytis cinerea* on *Vicia faba*

Fully developed, uniformly large leaves of *Vicia faba*, which have been sprayed dripping wet from a spraying device with a broth (0.1% content of active substance) prepared from an active substance formulated as a 10% wettable powder, were placed three at a time in Petri dishes lined with filter paper. When the leaves were dry again, they were infected with a freshly prepared, standardised spore suspension of the fungus (concentration: 100,000 spores/ml) and kept for 48 hours in a humid atmosphere at 20°C. After this time, the leaves displayed black, initially dot-shaped specks which rapidly spread. The number and size of the infected areas served as a yardstick for determining the effectiveness of the test substance.

b. Action afainst *Erysiphe cichoracearum* on *Cucumis sativus*

Young Cucumis sativus plants were sprayed with a spore suspension of the fungus after they had been sprayed with a 0.01% suspension of the active substance formulated as wettable powder and after the spray coating had dried. The degree of attack (extent of the leaf surface coated with the mycel coating) on the infected, treated leaves was assessed after 8 days in a greenhouse at approx. 23°C in comparison with untreated, infected controls.

c. Action against *Uromyces appendiculatus* on *Phaseolus vulgaris*

*Phaseolus vulgaris* plants in the 2-leaf stage were sprayed dripping wet with a suspension of the substance formulated as wettable powder (concentration: 0.1% of active substance). After the coating layer had dried, the plants were infected with a fresh spore suspension of bean rust and then kept for 1 day day in a humid chamber, then for 12 days in a greenhouse at 22°–22°C.

The number and size of the rust pustules served as a yardstick for evaluating the effectiveness of the test substances.

d. Action against *Phytophthora infestans* on *Solanum-Lycpersicum*

*S. Lycopersicum* plants of the same variety and in the same stage of development were sprayed with a broth of 0.1% active substance (prepared from the active substance formulated as a wettable powder). When dry, the plants were sprayed dripping wet with a zoospore suspension of *Ph. infestans*. They were then kept for 6 days in a greenhouse at 18°–20°C and high humidity (95–100%), after which time they displayed typical leaf specks. The evaluation of the tested substance was based on their number and size.

I claim:

1. A compound of the formula

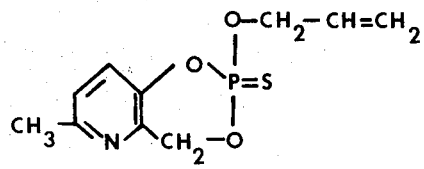

2. A compound of the formula

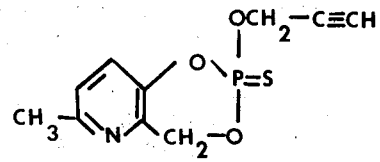

3. A compound of the formula

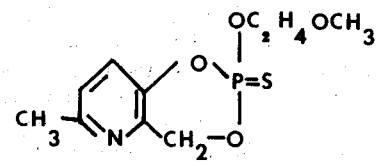

4. A compound of the formula

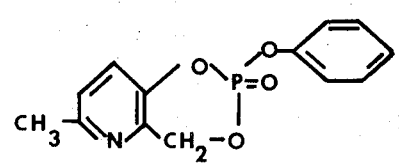

* * * * *